United States Patent [19]

Fruge'

[11] 4,394,355
[45] Jul. 19, 1983

[54] RECOVERY OF CATALYTICALLY-USEFUL COBALT AND LIKE METAL MOIETIES FROM THEIR SOLID OXALATES WITH EDTA SALTS

[75] Inventor: James D. Fruge', Pampa, Tex.

[73] Assignee: Celanese Corporation, New York, N.Y.

[21] Appl. No.: 354,251

[22] Filed: Mar. 2, 1982

[51] Int. Cl.$^3$ .................. C07C 51/235; C07C 55/07; C01G 51/00; C01G 3/00

[52] U.S. Cl. ........................................ 423/27; 423/49; 423/150; 562/531; 562/536; 562/566; 252/413

[58] Field of Search ............... 252/413; 562/531, 536, 562/597, 566; 423/27, 49, 150, 140, 35

[56] References Cited

U.S. PATENT DOCUMENTS

| | | | |
|---|---|---|---|
| 3,138,637 | 6/1964 | Lindstrom | 562/566 |
| 3,492,340 | 1/1970 | Aguilo | 562/597 |
| 3,634,070 | 1/1972 | Lindstrom | 423/35 |
| 3,780,096 | 12/1973 | Johnson | 252/413 |
| 3,840,469 | 10/1974 | Hobbs | 423/140 |
| 3,880,920 | 4/1975 | Wampfler | 252/413 |
| 4,246,185 | 1/1981 | Wood | 562/531 |
| 4,289,708 | 9/1981 | Scott | 562/531 |

Primary Examiner—Brian E. Hearn
Attorney, Agent, or Firm—Ralph M. Pritchett

[57] ABSTRACT

The solid oxalate of a catalytic metal such as cobalt, typically formed as an undesired and useless by-product during the liquid-phase oxidation of an organic compound, typically a hydrocarbon, in the presence of a homogeneous catalyst comprising said metal, is treated to convert the metal moiety to a reusable form by a process comprising leaching the metal oxalate with an aqueous solution of a soluble salt of ethylenediaminetetraacetic acid (EDTA). The resulting solution of EDTA-metal complex or chelate is then mixed with a soluble calcium salt to precipitate the oxalate moiety as insoluble calcium oxalate leaving the metal-EDTA complex in solution. After removing the resulting solid calcium oxalate, the remaining filtrate is acidified to convert the metal moiety to a simple salt which can be recycled to the liquid-phase oxidation, while the EDTA is precipitated as a solid which can also be recovered and re-used in the complexation step of the process.

9 Claims, No Drawings

RECOVERY OF CATALYTICALLY-USEFUL COBALT AND LIKE METAL MOIETIES FROM THEIR SOLID OXALATES WITH EDTA SALTS

BACKGROUND OF THE INVENTION

This invention relates broadly to a method for converting solid metal oxalates, insoluble compounds having little or no industrial use, to soluble salts useful especially as catalysts or as catalyst components in processes wherein an organic feedstock, usually a hydrocarbon and most commonly a paraffin hydrocarbon, is converted to one or more oxygenated derivatives by oxidation with molecular oxygen in a liquid phase containing a homogeneous catalyst comprising a metal such as cobalt, copper, or manganese. In particular, such processes are frequently conducted employing a lower carboxylic acid, especially acetic acid, as the reaction solvent with the organic feedstock being a lower alkane of about three to five carbon atoms, although liquid phase oxidations are also sometimes employed with alkanes or cycloalkanes having up to about eight carbon atoms. Closely-related processes comprise the liquid-phase oxidation of an aldehydoalkane, such as hexanal, heptanal, or nonanal, to form the corresponding carboxylic acid.

A commonly-encountered problem in such liquid-phase oxidation systems is the progressive deactivation of the catalyst by the reaction of the metal, e.g. cobalt, with oxalic acid (formed as an undesired reaction by-product) to form the insoluble oxalate, which is catalytically inert. This oxalate tends to precipitate on the interior surfaces of processing equipment containing the liquid reaction medium and/or streams, such as distillation residues, derived from it. Alternatively, the solid oxalate may also be present as a sludge in some of these process streams.

Until recent years, cobalt in its various industrially-useful forms (e.g., its soluble salts) has been available at moderate cost, so that mixing up the catalyst lost in the manner just described has not been a serious cost item. More recently, however, there have been sharp rises in the cost of cobalt. Additionally, there is the closely-related problem of increasing uncertainty concerning the availability of this strategically-important element in the industrialized world.

The art is already acquainted with one feasible method for recovering catalytically-useful cobalt salts from solid cobalt oxalate, this method being described in U.S. Pat. No. 3,840,469 to Hobbs et al. The heart of the patented process is the digestion of solid cobalt oxalate (normally in the form of a slurry) with a solution containing calcium ions whereby, calcium oxalate being even less soluble than cobalt oxalate in, for example, acetic acid, the oxalate moiety is converted to solid calcium oxalate while the cobalt moiety is solubilized and transferred into the liquid digestion medium as a dissolved cobalt salt. This cobalt salt can then be recycled to the liquid-phase oxidation system, with or without whatever additional processing may be desired (e.g., concentration), to replenish its catalyst content. The calcium oxalate is normally discarded.

Although the process of Hobbs et al. is workable and industrially useful, it has a drawback in that the digestion step employed in it has a mass-transfer limitation in the matter of replacing cobalt ions in the solid phase with calcium ions from the liquid phase; this difficulty attends practically all such digestions as employed, for example, in many laboratory procedures and is the reason for the common practice of allowing extended periods of time at elevated temperature for such digestions to be completed. Even after extended periods of time, of course, it is also realized both in the laboratory and in industry that such digestions are often still not complete because some material remains occluded within the solid particles.

It is an object of the present invention to provide a method for recovering cobalt from a solid comprising cobalt oxalate which is workable and which does not entail the step of digesting the solid with a calcium solution requiring, as just described, the replacement of cobalt ions in a solid with calcium ions. More particularly, it is an object of this invention to provide a method for expeditiously recovering cobalt moiety from solid cobalt oxalate which has been formed in the course of the liquid phase oxidation of an organic compound, especially a hydrocarbon and more especially an alkane, in the presence of a catalyst comprising cobalt and then returning the recovered cobalt to said liquid phase oxidation as makeup catalyst. Other objects of the invention will be apparent from the following specification and claims.

Although the process of the invention is especially directed at recovering cobalt, it will also be evident to those skilled in the art that it can be applied to other metals which are employed as catalysts in liquid phase oxidation, e.g. copper and manganese, so long as those metals are capable of being dissolved by chelating agents, the process of the invention being one which employs a chelation or complexation step as will be explained. For example, U.S. Pat. No. 4,246,185, to Wood, describes separating manganese and copper catalyst moieties from alkanoic acids having six to nine carbon atoms by treatment with oxalic acid to precipitate substantially all of the copper and manganese which are present as the oxalates which can then be filtered or centrifuged out of the alkanoic acid. The present invention can be employed, if desired, to recover the copper and manganese moiety from these oxalate precipitates followed by recycle of the recovered catalyst metal moieties to an oxidation step wherein the alkanoic acids are being formed by the liquid-phase oxidation of the corresponding aldehyde precursors of the alkanoic acids.

A related use of oxalic acid precipitation to recover cupric oxalate and manganese oxalate from alkanoic acids having three to nine carbon atoms is also described in copending application Ser. No. 065,239 filed Aug. 9, 1979 by R. H. Scott et al., and the presently-described method is also applicable in recovering and recycling the copper and manganese moiety which is separated as the oxalate salts from the alkanoic acids in that process.

The primary objective of the present invention is, however, its employment in the recovering of cobalt oxalate because cobalt is of particular economic and strategic importance.

BRIEF DESCRIPTION OF THE INVENTION

In accordance with the present invention, a solid comprising the oxalate of a metal of the group consisting of cobalt, copper, and manganese but especially cobalt is treated to recover said metal in the form of a solution of a simple salt of said metal (the term "simple salt" being employed to differentiate between a salt and a chelated complex) by leaching said solid with a solution of a chelating or complexing agent, especially a solution of the sodium salt of ethylenediaminetetraacetic acid (EDTA) whereby the metal moiety (i.e., cobalt, manganese, or copper) is solubilized as a complex with said chelating agent. Any insert solid which may have been present in admixture with, or comprising a solid substrate layer beneath, the metal oxalate remains as an undissolved solid residue from which the chelate-containing leach liquor is separated by an appropriate method such as filtration, centrifugation, or simple decantation. The separated leach liquor is then mixed with a solution containing calcium ions in a quantity which is at least stoichiometrically equivalent to the oxalate ions which, at this stage of the process, are now present in the leach liquor in dissolved form. For example, when the solid oxalate has been leached with sodium EDTA solution, the oxalate moiety will, by this stage of the process, have been converted into dissolved sodium oxalate.

When the leach liquor is mixed with the calcium salt solution, the calcium ions react with the oxalate ions to form the highly-insoluble calcium oxalate, which precipitates. The precipitate is then removed, as by filtration, leaving a clarified solution of the EDTA-metal complex. The clarified solution is then acidified, decomposing the complex to form solid EDTA. The solution now contains a simple salt of the metal which was previously present as the EDTA complex.

The solid EDTA is now filtered out of, or otherwise separated from, the acidified solution, and can now, if desired, be reconverted to the tetrasodium salt and recycled to the complexation step of the process. The dissolved metal salt remaining in the acidified liquid from which the EDTA has been removed can now be recycled, typically in the same solution, to be reused for its initial purpose, typically the catalysis of the liquid-phase oxidation of an organic feedstock such as a lower alkane or an aldehydoalkane to produce a carboxylic acid such as acetic acid.

Advantageously, the acidificaton step of the present process is preceded by a concentration step in which, immediately after separation of the solid calcium oxalate, the liquid is concentrated to at least about one percent metal content.

DETAILED DESCRIPTION OF THE INVENTION

Although there can be many circumstances in which it may be desired to recover a chelatable metal such as cobalt, copper, or manganese from a solid comprising the oxalate of that metal, such oxalates are, as a practical matter, encountered primarily in systems in which the metal, alone or in combination with another, has been used as homogeneous catalyst in the liquid-phase oxidation of an organic feedstock such as n-butane with molecular oxygen, in a reaction solvent such as acetic acid, to produce an oxygenated derivative of the organic feedstock, e.g. acetic acid. Typical of this type of process is that which is disclosed in U.S. Pat. No. 2,704,294 to Morgan and Robertson. Oxalate moiety appears in small amounts as an undesired by-product of such an oxidation and reacts with the cobalt which is present to form solid cobalt oxalate, which is catalytically useless and which also tends to form deposits on the interior of processing equipment, especially the bases and reboilers of distillation towers used to separate the oxidation product downstream from the reaction system. This fouling propensity is so pronounced that there has even been some experimentation with allowing, for example, the liquid reaction products after removal of light ends to flow through a packed bed of, for example, ceramic bodies to encourage the oxalate to collect at this point instead of being dispersed more widely through the processing apparatus.

As previously explained hereinabove, at least some method has already been developed to recover the cobalt in usable form from such systems in which the oxalate solid comprises an unwanted incrustation and/or sediment. It will also be noted from study of U.S. Pat. No. 3,840,469 that additional oxalic acid can be incorporated into those process residues and the like which already contain a quantity of cobalt oxalate for the purpose of completing the precipitation of all cobalt which may be present in such systems so that it can be collected at once as the solid oxalate, after which it is all reprocessed to recover the cobalt in a soluble and catalytically-useful form. A similar approach is taken with copper and manganese moiety in U.S. Pat. No. 4,246,185 issued Jan. 20, 1981 to Wood. The Wood patent deals with systems in which copper and manganese are used together to catalyze the oxidation of aldehydoalkanes of from six to nine carbon atoms as exemplified by hexaldehyde to form the corresponding monocarboxylic acids as exemplified by hexanoic acid in a liquid reaction medium comprising predominantly said aldehydes and said acids. In the reaction system contemplated by Wood the copper and manganese oxalates are not in themselves a very serious problem, but there is still need for an efficient method to recover the copper and manganese from the reaction medium for recycle to the oxidation step of the process. The invention claimed by Wood comprises essentially the deliberate addition of a quantity of oxalic acid for the purposes of recovering the copper and manganese from the liquid reaction product for the primary purpose of purifying the monocarboxylic acid product, recovery of the copper and manganese moieties in a reusable form being carried out, if desired, by the process of U.S. Pat. No. 3,840,469. Co-pending U.S. application Ser. No. 065,239 filed Aug. 9, 1979 by Scott el al., now U.S. Pat. No. 4,289,708, describes a technology similar to that of Wood, but dealing with a broader range of aliphatic monocarboxylic acids, i.e., acids having three to nine carbon atoms, using the same oxalic acid precipitation described by Wood.

With the exception of the possible use of a bed of inert solids as a deposition zone to collect insoluble oxalate as an encrustation on said inert solids, which is believed not to have been described previously in the literature and which is readily understandable once the idea has been briefly stated, the procedures by which the solid metal oxalate comes into being ready for processing to recover the metal moiety (cobalt, copper, or manganese) will be seen to be already understood from the prior art and is outside the scope of the present invention.

Accordingly, the following description deals with the handling of the solid metal oxalate while excluding the particulars of how it has been initially obtained, whether by the deliberate addition of oxalic acid so as to precipitate it from a liquid medium or whether, entirely or in part, it comprises an encrustation which has been deposited upon the interior surfaces of processing equipment or upon an inert bed of solids which has been provided so as to afford surfaces upon which the oxalate can deposit gradually over a period of time.

The first step of the present process is to leach the solid oxalate with an aqueous solution of the sodium salt of ethylenediaminetetraacetic acid (sodium EDTA). While concentration of this solution is not critical, it is useful to employ a concentration of about 3 wt % to 10%, typically 3%, calculated as EDTA moiety. At least about one molecule of EDTA but preferably 1.3 molecules of EDTA should be used per atom of chelatable metal known to be present in the oxalate-containing solid which is being leached. When the chelatable metal is cobalt, a 6.5:1 ratio of EDTA to cobalt, by weight, is recommended. When it is known how much metal oxalate is present, it is feasible to use an excess of EDTA based on previous experience with the same system. Alternatively it is possible, without resorting to chemical analysis, to leach the solids several times using a fresh sodium EDTA solution each time until a marked reduction in color of the leach liquor indicates that the leaching process is substantially complete. The leaching can be conducted at ambient temperature, but the rate of metal extraction from the solid is enhanced by using a warm leach solution, e.g. about 70° C.

When the solid oxalate is initially present as an encrustation on the interior of process equipment, e.g. distillation apparatus or a specially-provided solid deposition bed, it is especially advantageous to pump the warm leach solution through the apparatus, draining and then pumping more fresh solution until a low color level in the drained solution indicates that the leaching is substantially complete. In those instances in which the solid metal oxalate is in hand in the form of a filter cake or a concentrated slurry, as would be the case when it has been recovered by filtration, centrifugation, or sedimentation, the leaching step can be carried out by, for example, contacting the oxalate with the EDTA solution in a simple agitated vessel, with any remaining undissolved solid material then being removed, if desired, by filtration or centrifugation. Such a clarification or polishing step is not essential, however.

The leach liquor, either with or without the polishing step, is then mixed, preferably in an agitated vessel, with a soluble salt of calcium, introduced either as a solid or dissolved in any liquid which is inert toward the metal chelate. The calcium salt can be, as just described, any soluble one, although calcium chloride would not ordinarily be employed since it introduces a corrosive anion into the system. While other salts, for example the nitrate, can be used as desired, calcium acetate is, in most instances, especially useful and can be prepared by dissolving calcium hydroxide in acetic acid. This is especially the case when the present process is being used to recover catalyst metal moiety which has been employed in, and is to be recycled to, a liquid-phase oxidation process in which acetic acid is being used as reaction solvent or in which acetic acid is a reaction by-product. The concentration of calcium salt is not critical so long as the total amount of calcium which is introduced is sufficient to react stoichiometrically with all of the oxalate moiety which is present in the leach liquor. However, a saturated solution of calcium acetate in acetic acid, or in an acetic acid-water mixture, or in water is useful. The acetic acid, when it is employed, need not be glacial. As just described, the calcium salt solution is mixed with the EDTA-containing leach liquor in sufficient quantity that there is provided a quantity of dissolved calcium salt which is at least stoichiometrically equivalent to the oxalate moiety which is present. In recovering cobalt with calcium acetate, a 4:1 ratio of calcium acetate to cobalt, on the anhydrous basis, is convenient. The temperature is not critical and can be, for example, between about 25° C. and 70° C.

Calcium oxalate precipitates rapidly when the calcium salt solution is mixed with the leach liquor, usually as a fine-grained solid. The precipitated calcium oxalate is then removed, typically by filtration although one can also employ centrifugation, sedimentation, etc., and, after removal, preferably washed with 0.5 to 1.0 volume of wash liquid per unit volume of the calcium oxalate solid. The use of a filter aid like diatomaceous earth may be helpful. The wash liquid can be water or, alternatively, any other liquid such as acetic acid which is compatible with the liquid system in which the catalytic metal has been initially employed and to which it is contemplated that the metal will be returned after recovery. The washings are advantageously mixed with the clarified leach liquor which remains after separation of the calcium oxalate from it.

The clarified leach liquor, combined with the above-identified washings if desired, is then acidified with a strong acid, i.e., an acid strong enough that it will, upon admixture with the clarified leach liquor, reduce its pH sufficiently to cause precipitation of EDTA as a solid. To accomplish this precipitation, the pH should preferably be reduced to about 0.5 or below, typically to within the range of about 0.0 to 0.1. Any acid sufficiently acidic to accomplish this desired pH reduction can be used, but normally one would use a mineral acid; 70% nitric acid is especially useful. When the catalytic metal being recovered by the present process is cobalt, one should not use sulfuric acid for the acidification, since this will precipitate the cobalt as solid cobalt sulfate. A large excess of nitric acid at temperatures greater than 30° C. should be avoided as the EDTA is easily oxidized. The acidification step is advantageously conducted at whatever temperature obtains in the leach liquor after the calcium sulfate has been removed therefrom. The acid which is employed can be of any convenient concentration, either ordinary commercial strength or else, for convenience in handling, diluted with water down to a concentration of, for example, about 68%. The acidification can be conducted in any convenient apparatus, for example in a simple agitated vessel operating at atmospheric pressure.

As previously explained, the acidification results in precipitation of solid ethylenediaminetetraacetic acid, which is then separated from the acidified liquor by, for example, filtration, centrifugation, or sedimentation. Advantageously, the separated EDTA is then washed with water or with any liquid component of the liquid reaction medium in which the metal which is being recovered by the present process has been used as an oxidation catalyst and in which it will advantageously be recycled to the liquid-phase oxidation system from which the metal oxalate was initially withdrawn. The washings are conveniently combined with the acidified liquor.

The recovered solid EDTA is preferably reacted with sodium hydroxide to dissolve it and reconvert it to tetrasodium EDTA for re-use in the leaching step of the process. A useful concentration for the sodium EDTA solution which is to be returned to the leaching step is about 3% by weight. While the details of this reconversion of EDTA to sodium EDTA will be obvious to one skilled in the art, it is desirable to use a quantity of sodium hydroxide which is at least stoichiometrically equivalent to the EDTA which is being dissolved but not greatly in excess thereof. Advantageousely, one employs an excess of sodium hydroxide of about 3 to 5% over the theoretical stoichiometrical amount. A large excess of caustic should be avoided. The excess caustic reacts with cobalt to form cobalt hydroxide [$Co(OH)_2$, bright blue] which readily oxidizes in air to cobalt oxide [CoO, black]. The $Co(OH)_2$ and the CoO form a gelatinous precipitate which is lost in the oxalate removal filtration. The object in having a slight excess of caustic is to maintain a pH of about 12 in the leaching step.

Although it is not essential to the present process, it is frequently advantageous to concentrate the leach liquor just before the acidification step which has just been described. This concentration step, which can be conducted by using either simple evaporation or distillation, is preferably carried to the point of forming a concentrated liquid residue containing at least about 1% metal moiety (e.g. cobalt) by weight. Such a concentration step is not essential to the process, but it reduces the volume of the solution of, for example, cobalt which will subsequently be recycled to the liquid phase catalytic oxidation process in which the metal is being employed as oxidation catalyst.

With or without the intermediate concentration step just described, the acidified leach liquor, now substantially free of EDTA, comprises a solution of the catalytic metal which was initially present as solid oxalate, now in the form of a simple salt the anion of which will be derived from the mineral acid employed in the acidification and/or any carboxylic acid which may have been present in the liquids used up to this point in the process (i.e., frequently acetic acid.) This metal salt solution can be, of course, withdrawn at this point for whatever use may be contemplated for it, but normally it will be recycled as catalyst makeup to the liquid-phase oxidation process in which the metal, e.g. cobalt, is being employed as catalyst or as part of the catalyst system.

The following example is given by way of illustration. It will be understood that many variations can be made therefrom within the scope of the invention. In particular, the recovery of cobalt will be exemplified, but it will be understood that the process can also be applied to copper and manganese.

EXAMPLE 1

A solution of tetrasodium ethylenediaminetetraacetate was prepared by mixing 8.0033 grams of solid ethylenediaminetetraacetic acid with 250 ml $H_2O$ and about 10.5 grams of a 50% aqueous solution of sodium hydroxide. This mixture includes sufficient sodium to provide a pH at least 12 (actual pH was 13.1) in the resulting solution of sodium EDTA. A large excess of caustic was avoided, because excess caustic will, in the next step of the process, react with cobalt to form cobalt hydroxide which readily oxidizes in the presence of air to the oxide. The hydroxide and the oxide form a gelatinous precipitate which can constitute a substantial cobalt loss in the process. This EDTA-solution step of the process is conducted advantageously at about 68° C.

To approximately 260 grams of the sodium EDTA solution as prepared above there was added, with agitation, 3.8612 grams of cobalt oxalate at a temperature of about 68 degrees °C. Relatively high temperatures, e.g. around 97° C., are avoided because they increase the process loss to cobalt hydroxide. Ambient temperature of around 30° C. can be used if desired, but about 70° C. is recommended.

After approximately 10 minutes of agitation of the cobalt oxalate with the sodium EDTA solution, substantially all of the solid had been dissolved.

To the cobalt-EDTA complex solution prepared above there was then added approximately 4 grams of solid calcium acetate. The quantity of calcium acetate which was added was sufficient to precipitate all of the oxalate moiety present in the solution, with approximately a 10% excess of calcium over the amount stoichiometrically required for this precipitation. Calcium oxalate resulting from reaction of the calcium acetate with the dissolved oxalic acid present in the solution was of a very small particle size, i.e. less than 2 microns. Accordingly, diatomaceous earth filter aid was mixed into the reaction mixture before filtration.

The reaction mixture containing the diatomaceous earth was then filtered under vacuum to remove the solid calcium oxalate. The solid accumulated on the filter was washed twice with about 10 ml of water. The calcium oxalate and filter aid were discarded.

The clarified filtrate, now containing the cobalt in solution as the EDTA:cobalt complex, was then concentrated under vacuum for about 75 minutes (approximately 213 mm Hg absolute pressure) until the cobalt content, calculated as cobalt ion, was approximately 1 to 2% by weight. The liquid temperature at the end of this concentration step was approximately 73°-74° C. Evaporation at atmospheric pressure can also be employed if desired. In this example, the evaporation was conducted batchwise, but it can also be conducted continuously in conventional evaporation apparatus.

The liquid residue from the evaporation step was then acidified by dropwise addition, with stirring, of aqueous 50% nitric acid solution until the pH had been reduced from pH 12.7 to pH 1, resulting in the precipitation of crystals of EDTA. Additional quantities of nitric acid were added, in an amount to reduce the pH further to about 0.1, during the course of which further acidification more crystals of EDTA were precipitated. The use of excess nitric acid is avoided, especially at temperatures greater than 30° C., to avoid oxidation of the EDTA. In the present example the acidification step was conducted at approximately 30° C. and approximately 9.5 parts by weight of nitric acid (100% basis) were used per part of cobalt in the solution being acidified. It will be understood that any excess sodium hydroxide which may be present in the solution will require a corresponding increase in nitric acid to neutralize it in addition to decomposing the cobalt:EDTA complex.

Acidification of the solution as described above results in precipitation of free ethylenediaminetetraacetic acid as a solid, which is then filtered out and reworked if desired to prepare a solution of sodium EDTA for reuse as previously explained.

The solution remaining after filtering out the solid EDTA consists essentially of cobaltous nitrate and acetate in a liquid consisting essentially of about 99% water. It is suitable, with or without additional concentration if desired, for use as catalyst makeup in a process for oxidizing an organic feedstock, e.g. a lower alkane, cycloalkane, or aldehydoalkane, in a solvent comprising a carboxylic acid such as acetic acid to produce an oxygenated derivative thereof such as acetic acid.

Chemical analysis of the solution of cobalt salts obtained after filtering out the solid EDTA and lightly washing the EDTA with water with the washings being combined with the main body of the filtrate indicated that, of the cobalt originally contained in the cobalt oxalate introduced into the chelation or complexation step of the process as described above, approximately 96% had been recovered as dissolved cobalt salts in the solution.

The embodiments of the invention in which an exclusive claim or privilege is claimed are:

1. In a process for treating a solid comprising the oxalate of a metal of the group consisting of cobalt, copper, and manganese to recover therefrom an aqueous solution containing a water-soluble salt of said metal substantially free from oxalate moiety, the improvement which comprises:

leaching said solid with an aqueous solution of a water-soluble salt of ethylenediaminetetraacetic acid (EDTA) to form a leach liquor containing in solution the metal moiety of said metal oxalate in the form of the EDTA-metal complex;

mixing said leach liquor with a solution containing dissolved calcium ions in a quantity at least stoichiometrically equivalent to the oxalate ions contained in said leach liquor to form a mixture comprising a precipitate of solid calcium oxalate and a solution containing said EDTA-metal complex;

separating said calcium oxalate precipitate from said mixture to produce a clarified solution of said EDTA-metal complex;

acidifying said clarified solution with an effective amount of a strong acid to decompose said complex to form solid EDTA and a dissolved salt of said metal; and removing said solid EDTA from said acidified solution leaving said metal salt dissolved therein.

2. The improvement of claim 1 wherein said solid comprising a metal oxalate comprises solid cobalt oxalate.

3. The improvement of claim 1 wherein said strong acid is a mineral acid other than sulfuric and wherein said metal is cobalt.

4. The improvement of claim 3 wherein said mineral acid is nitric acid.

5. The improvement of claim 2 wherein said solution containing dissolved calcium ions is calcium acetate dissolved in a liquid comprising predominantly acetic acid.

6. The improvement of claim 2 wherein said step of acidifying said clarified solution comprises adjusting the pH to about 0.0 to 0.5.

7. The improvement of claim 6 comprising the additional step of concentrating said clarified solution to a cobalt concentration of at least about 1% by weight after said separation of calcium oxalate precipitate and before said acidification step.

8. In a process for oxidizing an organic feedstock with a catalyst comprising cobalt in a liquid phase comprising a carboxylic acid to produce a liquid oxidate comprising a carboxylic acid and wherein cobalt initially contained in said catalyst is converted to cobalt oxalate, in which process said cobalt oxalate is separated as a solid from said oxidate and converted to a cobalt salt which can be re-used as catalyst in said process, the improvement which comprises;

leaching said solid with an aqueous solution of a water-soluble salt of ethylenediaminetetraacetic acid (EDTA) to form a leach liquor containing in solution the cobalt moiety of said cobalt oxalate in the form of the EDTA-cobalt complex:

mixing said leach liquor with a solution containing a quantity of calcium ions sufficient to react with said complex to form a mixture comprising a precipitate of solid calcium oxalate and a solution containing said EDTA-cobalt complex;

separating said calcium oxalate precipitate from said mixture to produce a remaining clarified solution of said EDTA cobalt complex;

acidifying said clarified solution with an effective amount of a strong acid other than sulfuric acid to decompose said complex to form solid EDTA and a dissolved cobalt salt;

removing said solid EDTA from said acidified solution leaving a clarified cobalt salt solution; and returning said clarified cobalt salt solution to said oxidation process for re-use as catalyst therein.

9. The improvement of claim 8 wherein said organic feedstock is an alkane or an aldehydoalkane and wherein said carboxylic acid is an oxygenated derivative of said alkane or aldehydoalkane.

* * * * *